United States Patent [19]
Wenstrom, Jr.

[11] Patent Number: 5,522,845
[45] Date of Patent: Jun. 4, 1996

[54] BONE ANCHOR AND BONE ANCHOR INSTALLATION

[75] Inventor: Richard F. Wenstrom, Jr., Attleboro, Mass.

[73] Assignee: Mitek Surgical Products, Inc., Westwood, Mass.

[21] Appl. No.: 312,894

[22] Filed: Sep. 27, 1994

[51] Int. Cl.⁶ .................................................. A61B 17/04
[52] U.S. Cl. ......................... 606/232; 606/72; 606/78
[58] Field of Search ........................ 606/232, 72–77, 606/104, 78

[56] References Cited

U.S. PATENT DOCUMENTS

| | | | |
|---|---|---|---|
| 5,207,679 | 5/1993 | Li | 606/232 |
| 5,217,486 | 6/1993 | Rice et al. | 606/232 |
| 5,358,511 | 10/1994 | Gatturna et al. | 606/232 |

*Primary Examiner*—Gary Jackson
*Attorney, Agent, or Firm*—Pandiscio & Pandiscio

[57] ABSTRACT

A bone anchor and a bone anchor installation tool for deploying the bone anchor in bone.

11 Claims, 15 Drawing Sheets

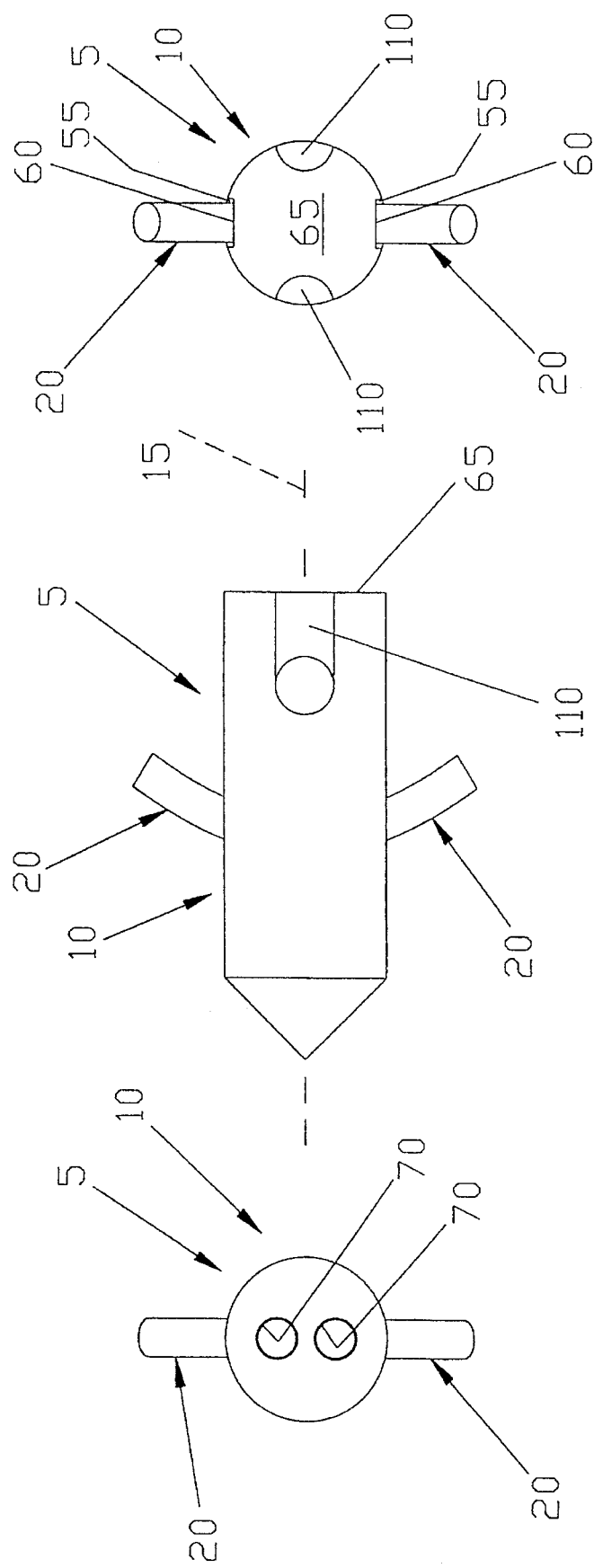

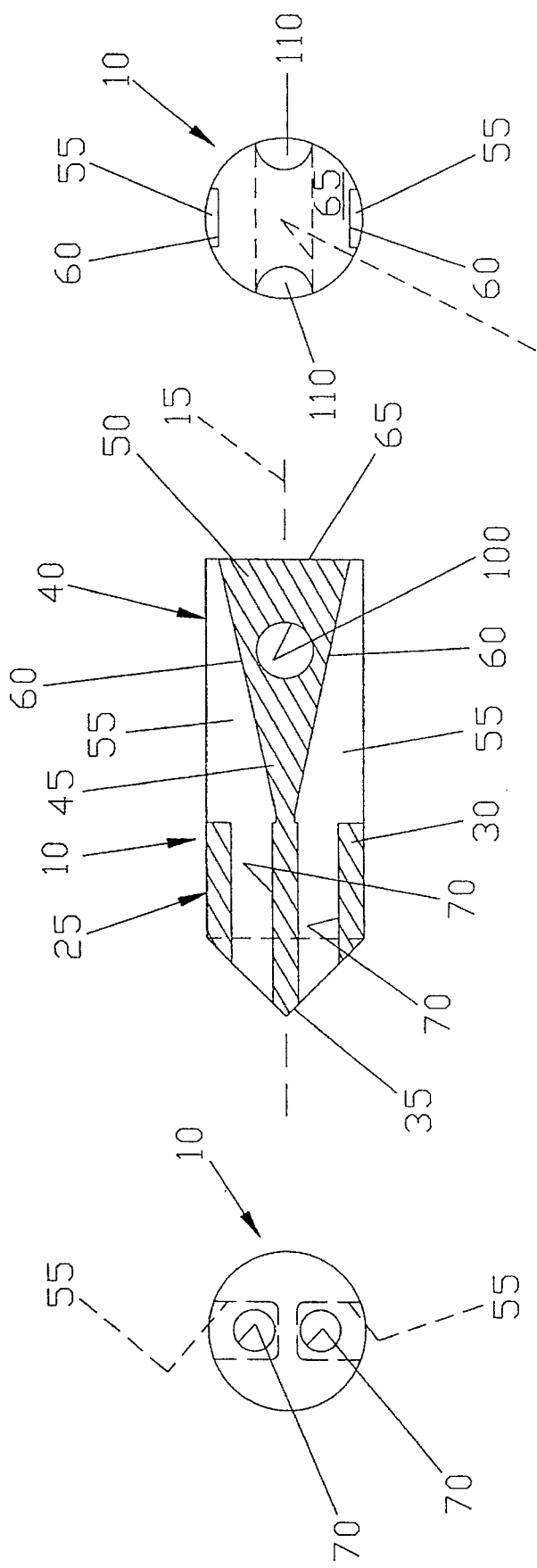

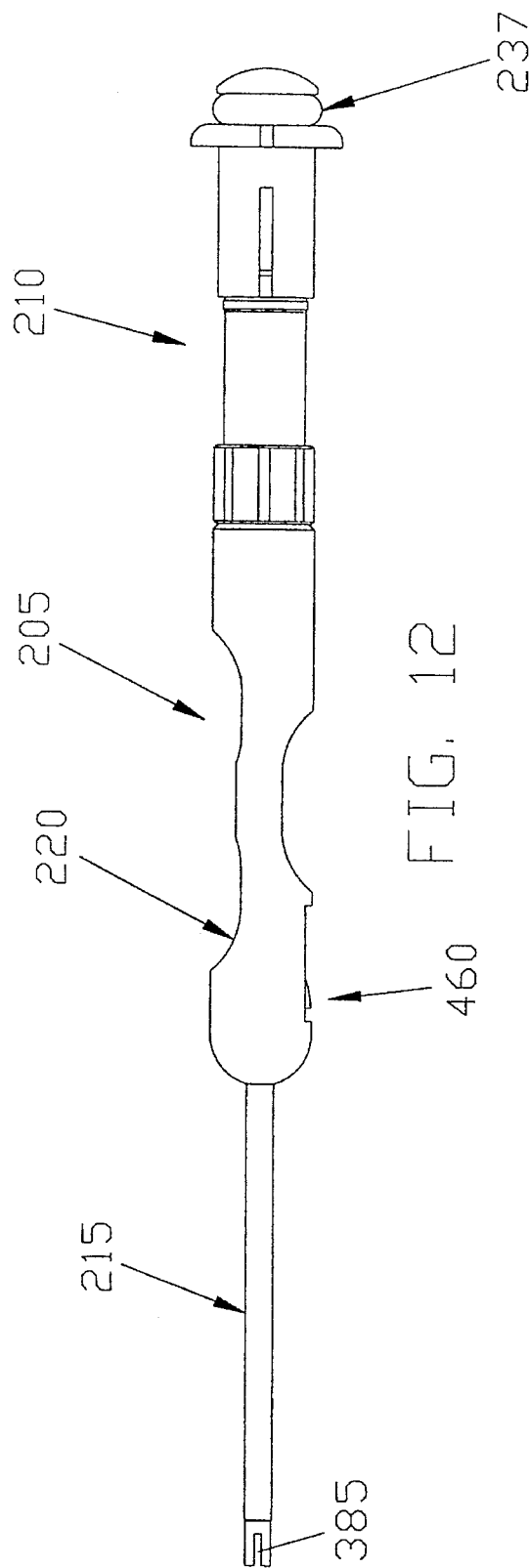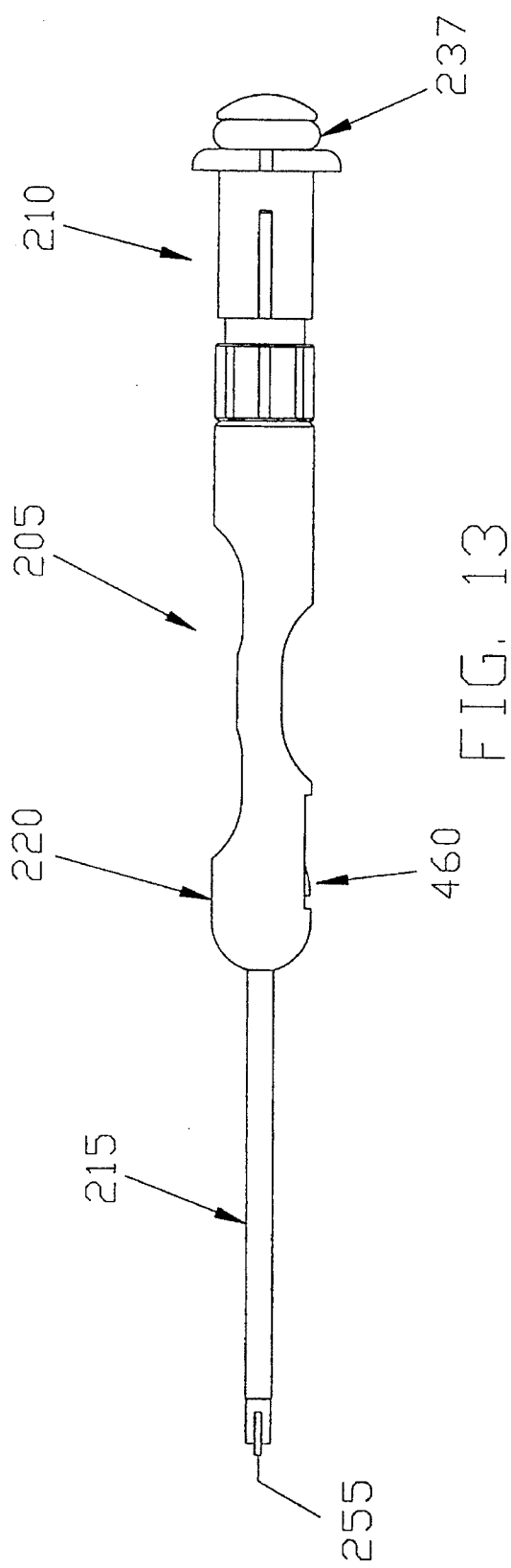

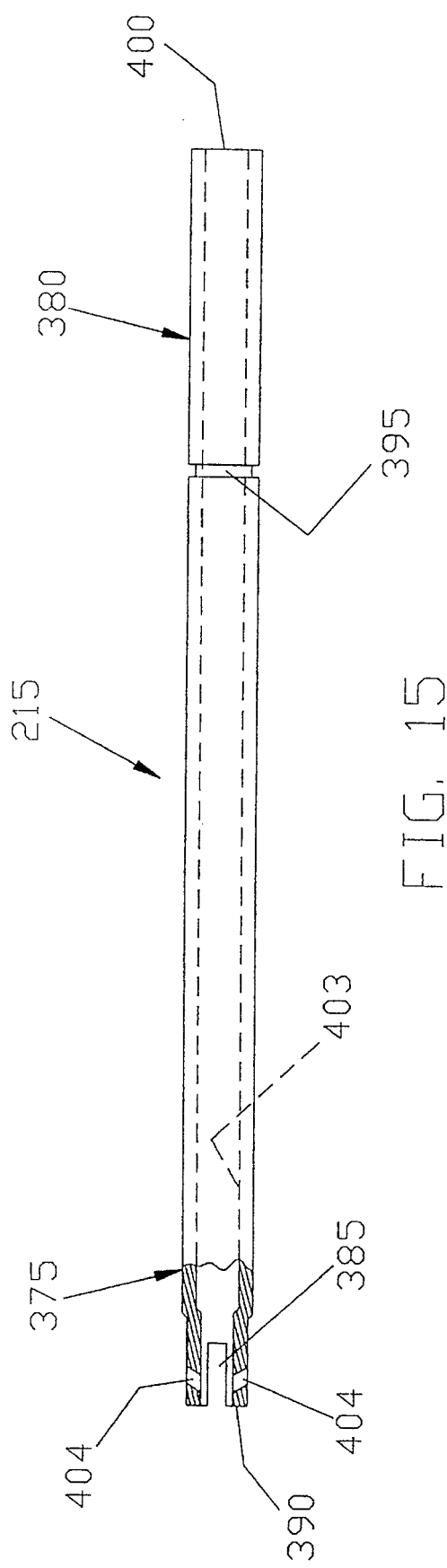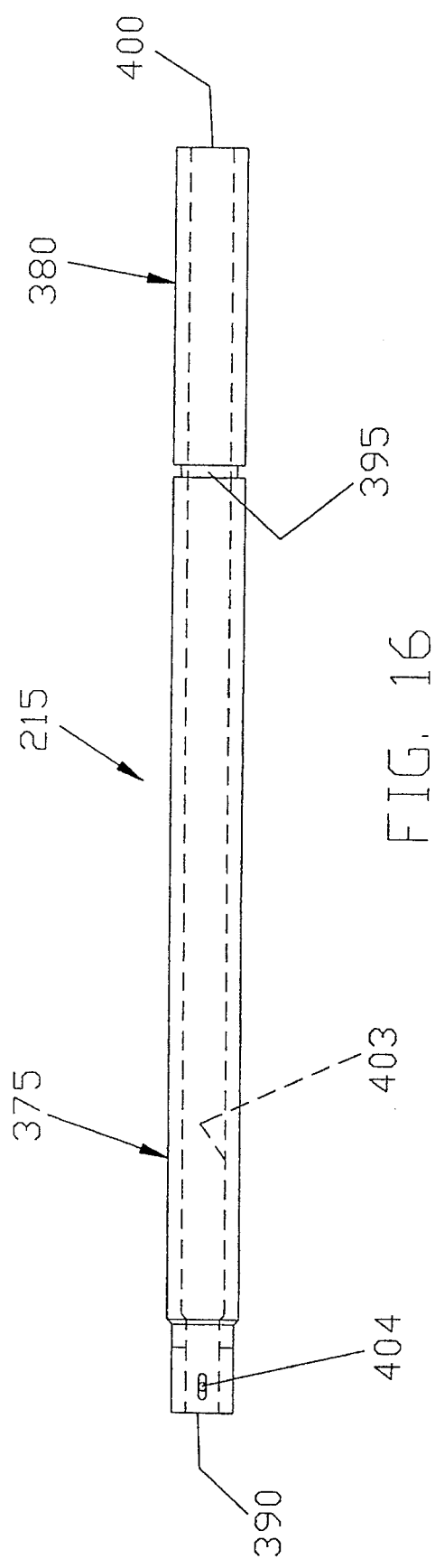

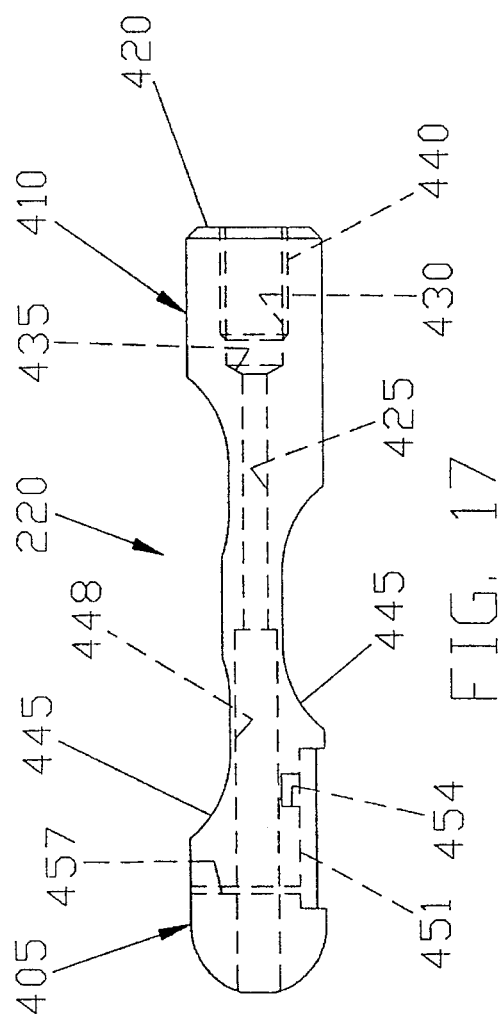
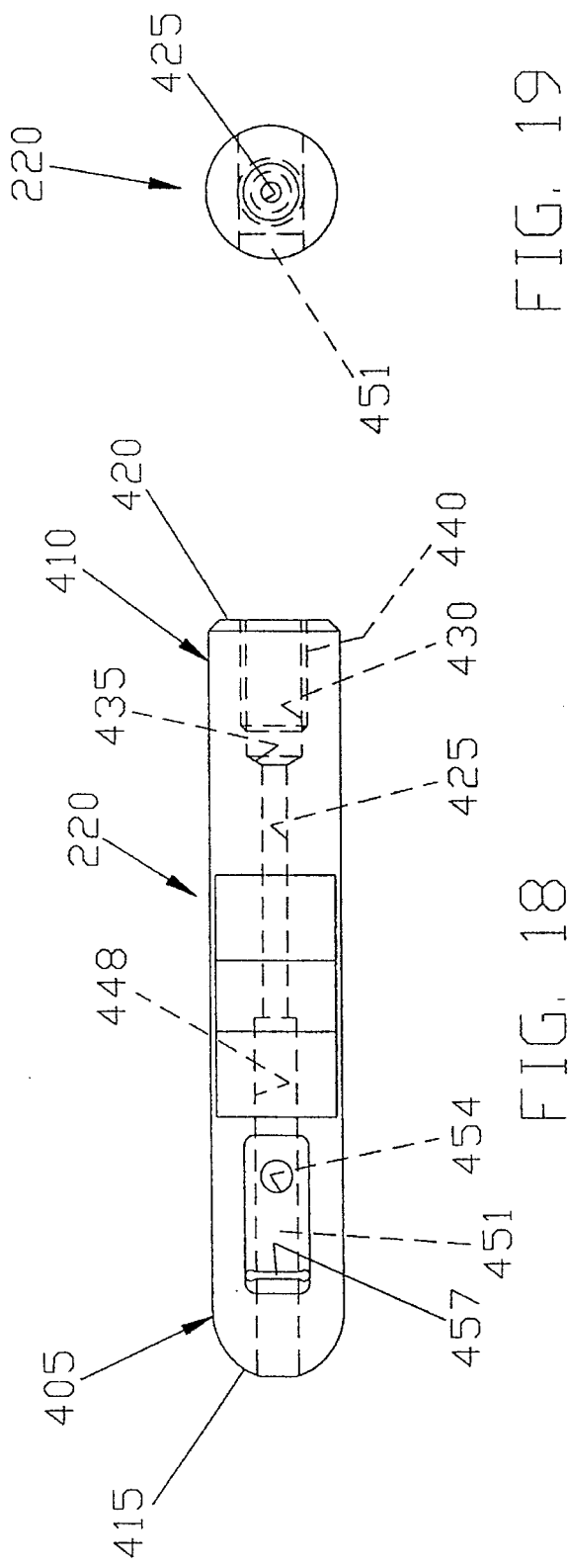
FIG. 17
FIG. 18
FIG. 19

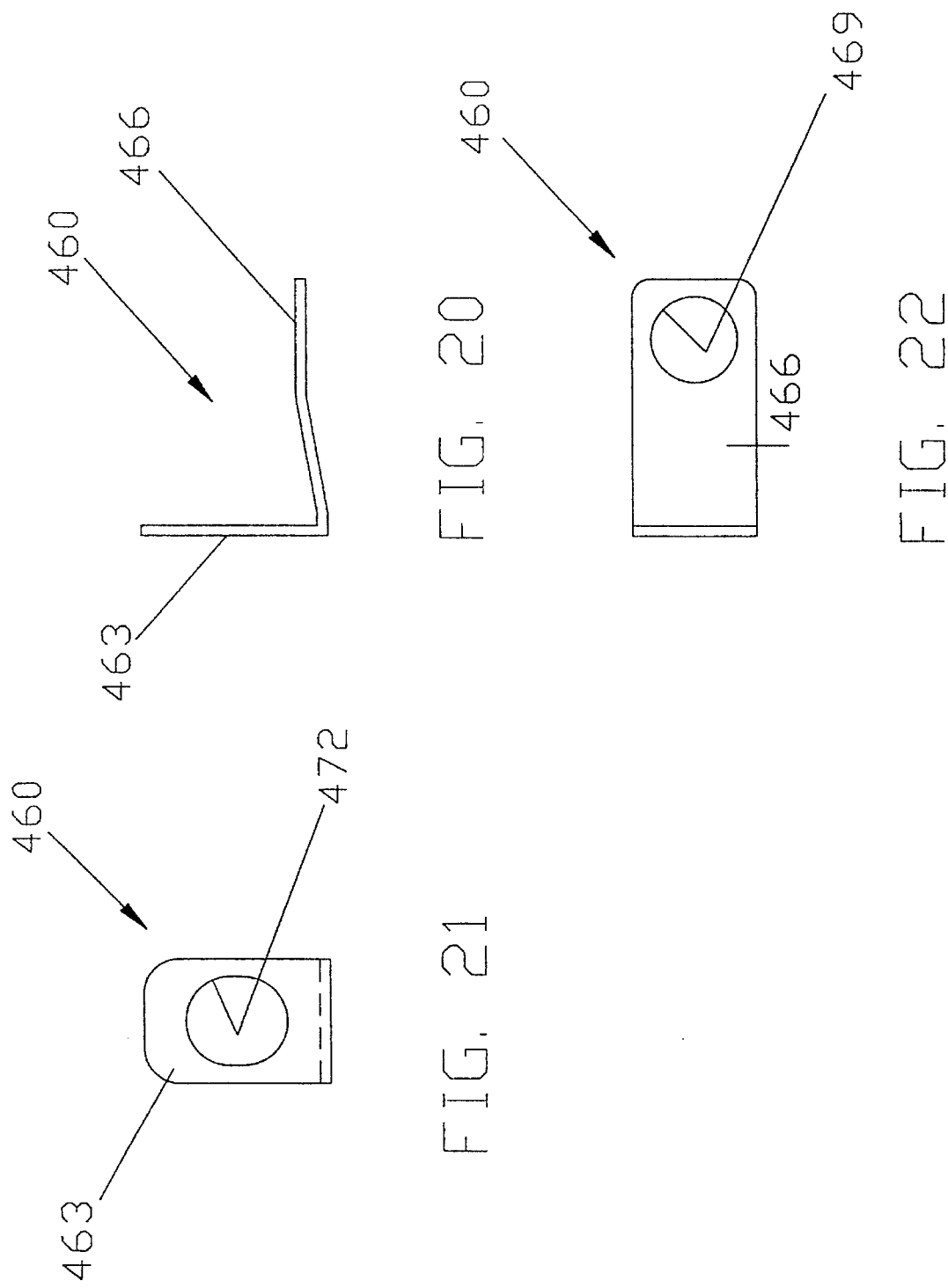

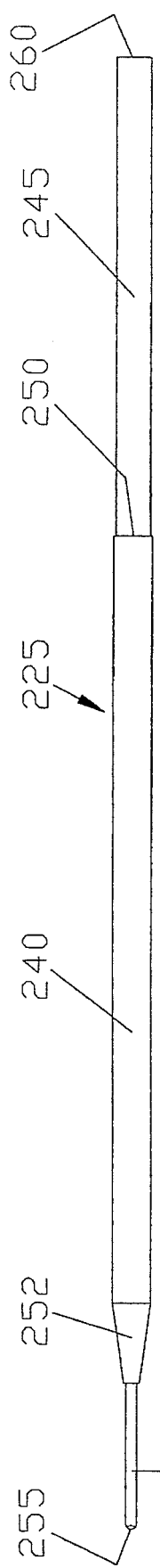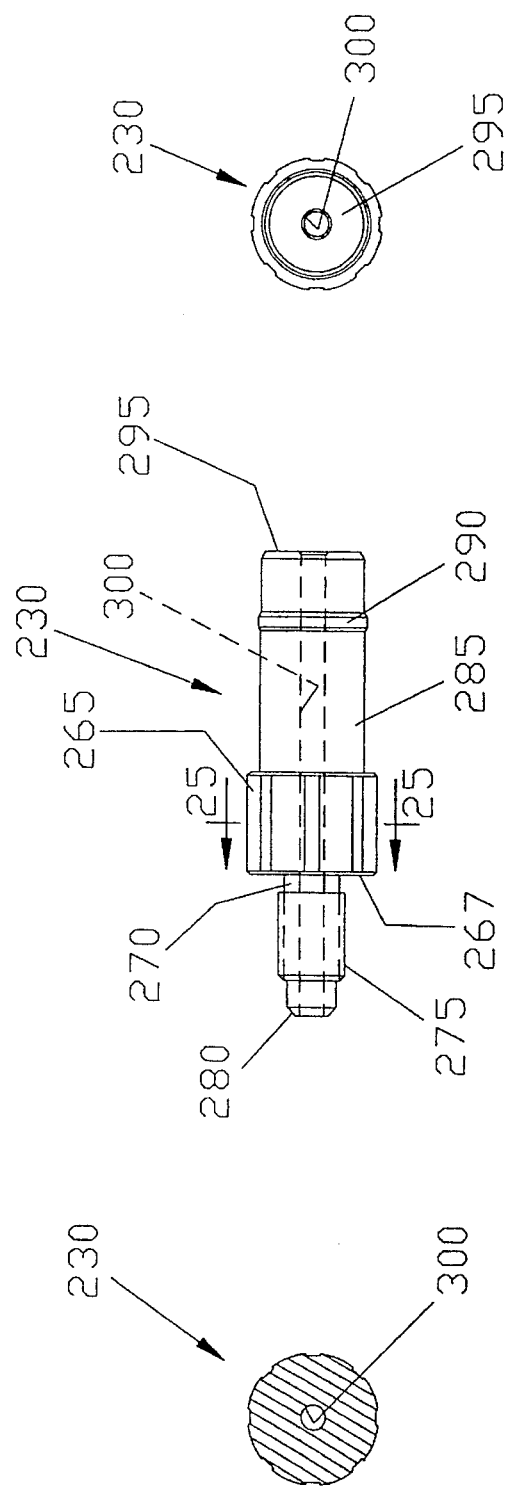
FIG. 23
FIG. 24
FIG. 25
FIG. 26

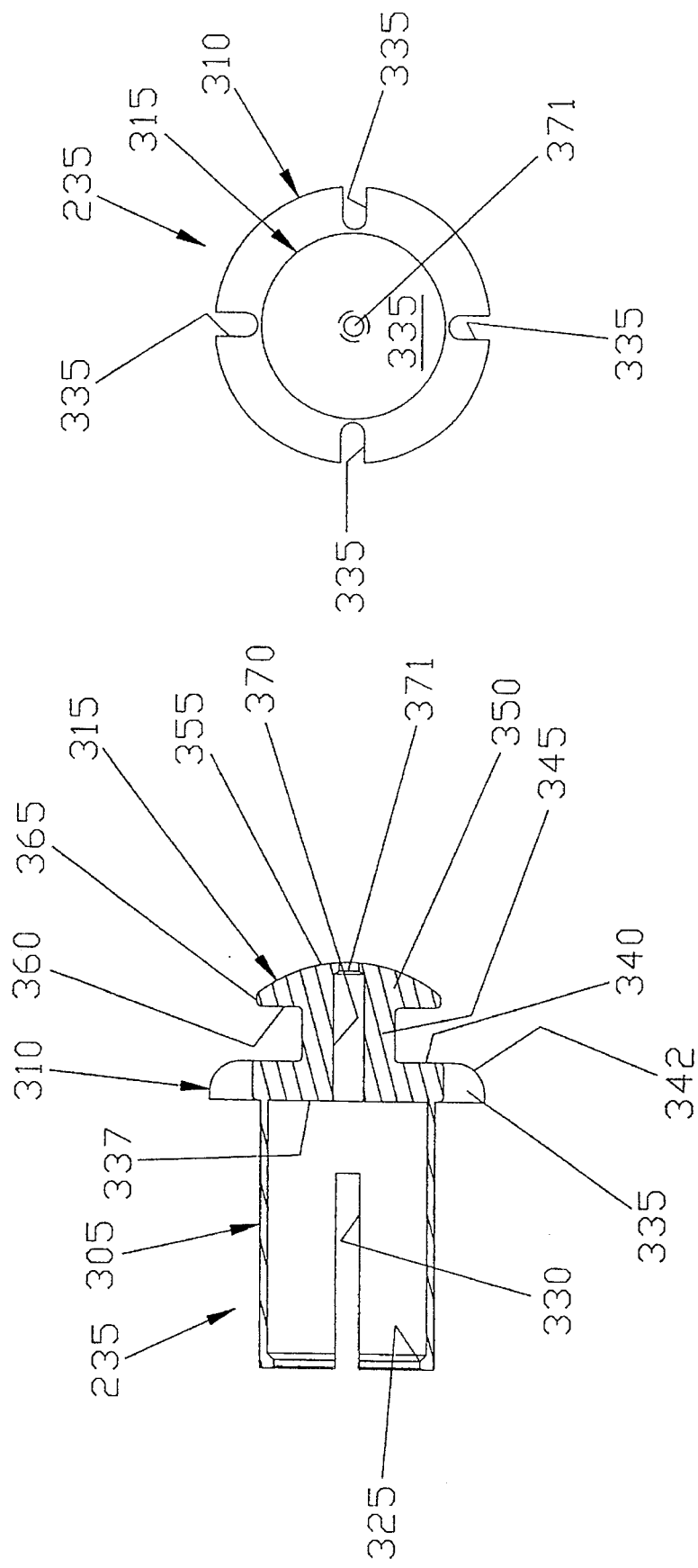

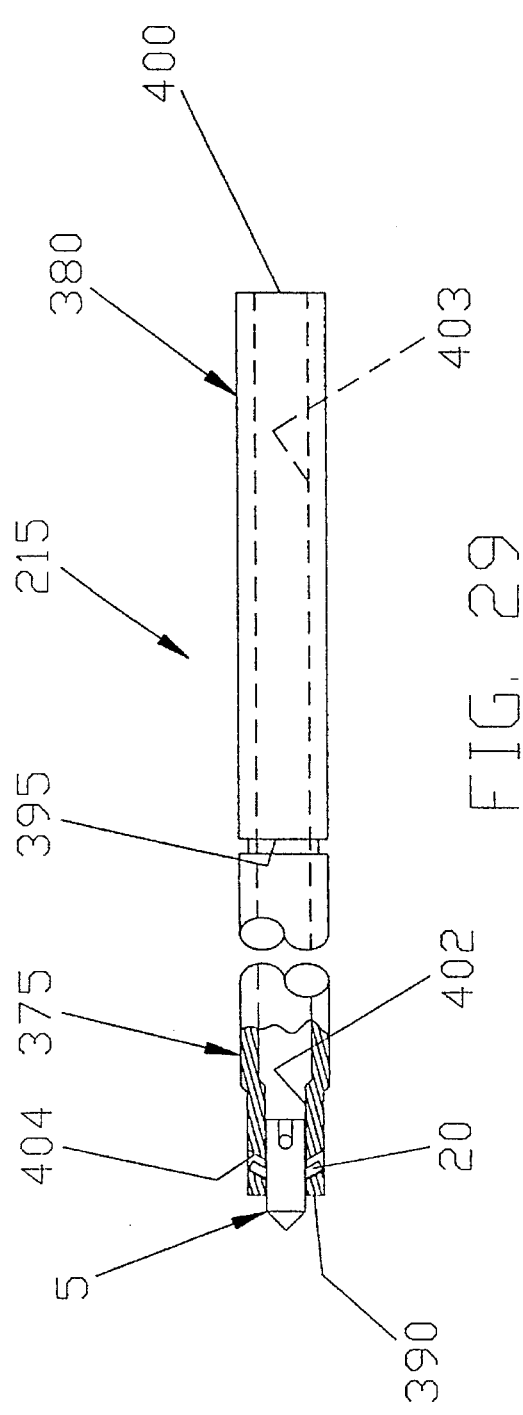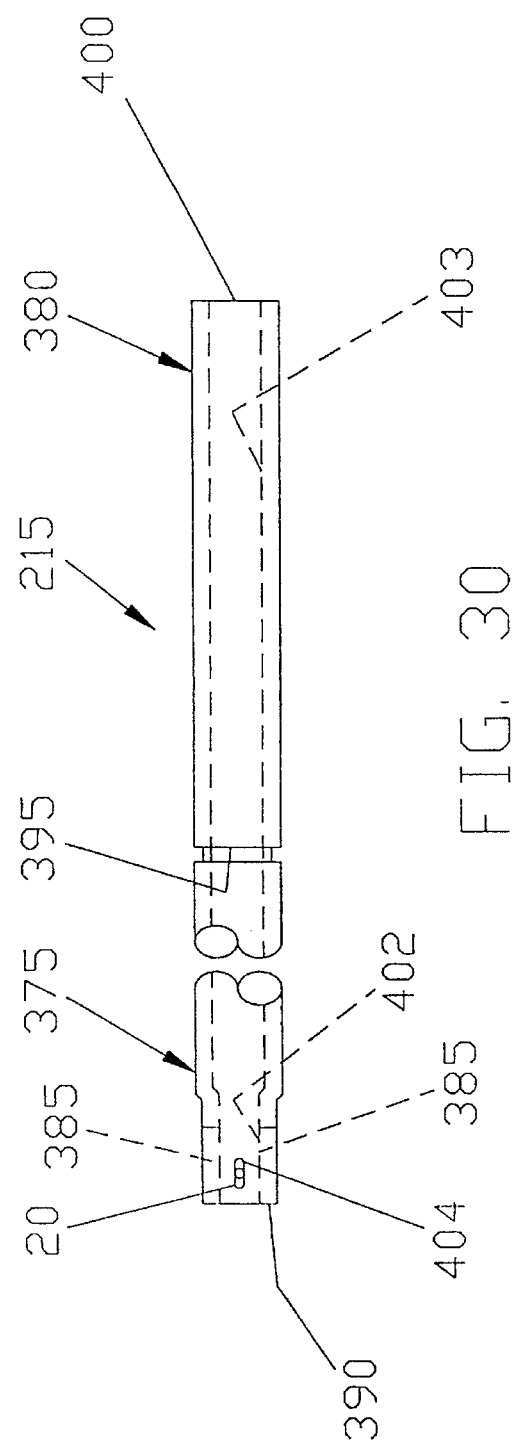

BONE ANCHOR AND BONE ANCHOR INSTALLATION

FIELD OF THE INVENTION

This invention relates to surgical devices in general, and more particularly to devices for attaching suture, bone and/or soft tissue to bone.

BACKGROUND OF THE INVENTION

Bone anchors for attaching suture, bone and/or soft tissue to bone are well known in the art. See, for example, U.S. Pat. Nos. 4,898,156; 5,046,513; 5,192,303; 4,899,743; 4,968,315; 4,946,468; 5,002,550; 5,207,679; and 5,217,486; and U.S. patent applications Ser. Nos. 07/981,011; 08/075,168; 08/030,657; 08/197,927; 08/098,599; and 08/180,425.

Installation tools for deploying such bone anchors in bone are also well known in the art. See, for example, the foregoing U.S. patents and patent applications.

Complete details of the construction and operation of the foregoing exemplary bone anchors and bone anchor installation tools are provided in the above-identified patents and patent applications, which patents and patent applications are hereby incorporated herein by reference.

While the bone anchors disclosed in the foregoing U.S. patents and patent applications have proven more than satisfactory for most applications, it has been noted that certain problems can occur when using these bone anchors in special situations.

More particularly, with some of the foregoing bone anchors (e.g. the anchors disclosed in U.S. Pat. Nos. 5,207,679 and 5,217,486), it can be very difficult to form the bone anchors in a very, very small size, e.g. bone anchors having a length on the order of 3.7 millimeters or so. This is because the maximum radius of curvature which can be imparted to the anchor's barbs is limited by the characteristics of the material out of which the barbs are formed. When using pseudoelastic materials of the sort preferred for forming the barbs, this consideration can become significant as the size of the anchor is reduced to the point where the anchor has a length on the order of 3.7 millimeters or so. In particular, as one progressively reduces the size of the barb after the maximum radius of curvature has been encountered, the overall length of the barb must necessarily decrease. Accordingly, less barb material is available for secure attachment to the anchor body and/or less barb material is available for engaging the surrounding bone during anchor deployment.

Furthermore, while the bone anchor installation tools disclosed in the foregoing U.S. patents and patent applications have proven more than satisfactory for most applications, it has been noted that certain problems can occur when using these installation tools in special situations.

More particularly, with some of the foregoing installation tools (e.g. the installation tools disclosed in U.S. Pat. Nos. 4,898,156; 5,046,513; 5,192,303; and 4,899,743), the portion of the tool which carries the anchor (i) is wider than the body of the anchor itself, and (ii) must be positioned within the bone during anchor deployment. As a result of this construction, the bone hole must be formed significantly larger than the body of the anchor in order to permit anchor deployment. This can be a disadvantage in certain situations where it may be necessary to form the smallest possible hole in the bone.

With others of the foregoing installation tools (e.g. the installation tools disclosed in U.S. Pat. No. 5,217,486 and U.S. patent application Ser. No. 08/098,599), the portion of the tool which carries the anchor does not need to be received by the bone during anchor deployment. Instead, only a relatively thin drive pin enters the bone during anchor deployment. The drive pin is formed so that it has a diameter less than the diameter of the anchor body. As a result of this construction, the bone hole can be formed so that it has substantially the same width as the anchor body. However, it has also been found that where the installation tool is being used to set extremely small bone anchors, the drive pin must be so thin that it may bend or otherwise deform in certain circumstances. When this occurs, it may affect anchor deployment and/or render the installation tool unusable for subsequent anchor deployments.

In addition to the foregoing, it has also been found that where the installation tools are being used in conjunction with anchors adapted to attach suture to bone, it can be very helpful to provide suture management means for controlling the disposition of the one or more free suture ends. In this respect it is noted that with some of the foregoing installation tools (e.g. the installation tools disclosed in U.S. Pat. Nos. 4,946,468 and 5,002,550), such suture management means are provided. While such suture management means work well enough for most applications, it has been found that alternative suture management means could be helpful in some situations.

Furthermore, as the overall size of a bone anchor is decreased, it becomes less and less practical for the bone anchor to be mounted to the installation tool in the field (e.g. the operating room). Instead, it becomes necessary to mount the bone anchor in the installation tool at the point of manufacture. However, with the bone anchor installation tools of the type disclosed above, this means that the installation tool cannot easily be reused to deploy a subsequent anchor. Thus, with bone anchor installation tools of the sort disclosed above, the installation tool must generally be made so as to be disposable when it is to be used with a very, very small anchor. This can be undesirable in many circumstances.

Additionally, as the overall size of the bone anchor is decreased, it becomes more important to provide additional means for ensuring that the bone anchor does not become separated from the installation tool prior to deployment of the bone anchor in bone.

OBJECTS OF THE INVENTION

Accordingly, one object of the present invention is to provide an improved bone anchor. Another object of the present invention is to provide an improved bone anchor which can be formed in a very, very small size, e.g. on the order of 3.7 millimeters or so in length.

A further object of the present invention is to provide an improved bone anchor, wherein the bone anchor uses a new barb configuration so as to permit the bone anchor to be formed very, very small, yet provides sufficient barb material for secure attachment to the anchor body and for engaging the surrounding bone during anchor deployment.

Yet another object of the present invention is to provide an improved bone anchor of the sort adapted to anchor suture to bone.

Still another object of the present invention is to provide an improved bone anchor installation tool.

Another object of the present invention is to provide an improved bone anchor installation tool, wherein the installation tool is adapted to deploy bone anchors of the type adapted to anchor suture to bone.

A further object of the present invention is to provide an improved bone anchor installation tool, wherein the installation tool is adapted to provide improved suture management means for managing the free end or ends of a suture or sutures attached to the bone anchor.

Yet another object of the present invention is to provide an improved bone anchor installation tool, wherein the installation tool is relatively easy to manufacture and relatively inexpensive to produce.

Still another object of the present invention is to provide an improved bone anchor installation tool, wherein the installation tool is adapted to deploy very, very small suture anchors.

Yet another object of the present invention is to provide an improved bone anchor installation tool, wherein the installation tool is adapted to permit a suture anchor to be attached to a portion of the tool at the point of manufacture, with this portion of the tool being attachable to another portion of the installation tool in the field (e.g. in the operating room).

And another object of the present invention is to provide additional means for ensuring that the bone anchor does not become separated from its seat on the installation tool prior to the deployment of the bone anchor in bone.

Still another object of the present invention is to provide a novel method for deploying a bone anchor in bone.

SUMMARY OF THE INVENTION

These and other objects of the present invention are achieved through the provision and use of a novel bone anchor and a novel bone anchor installation tool.

The novel bone anchor includes a housing, at least two barbs, and suture attachment means for attaching one or more lengths of suture to the bone anchor.

The housing has a longitudinal axis and includes a distal portion having an inner end and an outer end, and a proximal portion having an inner end and an outer end. The inner end of the distal portion is connected to the inner end of the proximal portion. The housing has a maximum cross-section, as measured transverse to its longitudinal axis, which is slightly smaller than the diameter of the hole in the workpiece within which the anchor is to be deployed. At least two equally-circumferentially-spaced longitudinal channels extend from the inner end of the proximal portion to the outer end of the proximal portion. The depth of these longitudinal channels gradually decreases as the channels extend from the inner end of the proximal portion to the outer end of the proximal portion. Each of the longitudinal channels also has an associated bore communicating therewith. Each of these bores extends from the inner end of the distal portion (where it communicates with its associated longitudinal channel) toward the outer end of the distal portion.

The bone anchor's at least two barbs extend in equally-circumferentially-spaced relation to each other, with one end of each barb being disposed in a bore and the other end of the barb being substantially radially displaced from the housing, whereby each barb will be aligned with and extend out of one longitudinal channel. Each barb is curved in its normal unstressed state, but is capable of being elastically deformed to a substantially straight configuration. More particularly, each barb comprises three distinct curves so as to assume a handlebar configuration when in its normal unstressed state. Each barb is attached to the housing by forcing half of the barb into a bore and allowing the other half of the barb to protrude out of a corresponding channel.

The suture attachment means are formed in the proximal portion of the housing. In a preferred embodiment, the suture attachment means comprise a round or elongated hole extending diametrically through the proximal portion of the housing, adjacent its outer end and through the regions of the proximal portion which are located between the longitudinal channels.

The foregoing anchor is intended to be used in conjunction with a novel installation tool.

In one form of the invention, the installation tool comprises:

a body having a distal portion and a proximal portion, the distal portion terminating in a distal end surface and the proximal portion terminating in a proximal end surface, and further wherein an axial passageway extends between the distal end surface and the proximal end surface, with the distal end of the axial passageway being sized to receive at least a portion of a bone anchor therein, and further wherein at least two lateral passageways extend through the body so as to intersect the axial passageway, whereby each of the bone anchor's barbs will be received by one of the lateral passageways when the bone anchor is disposed in the distal end of the axial passageway; and a shaft slidably disposed in the axial passageway, the shaft terminating in a distal end surface and being adapted to move between (i) a first retracted position wherein the shaft's distal end surface is withdrawn sufficiently far into the interior of the axial passageway so as to allow at least a portion of a bone anchor to be received within the distal end of the axial passageway, and (ii) a second extended position wherein the shaft's distal end surface projects out of the distal end of the axial passageway.

The installation tool also preferably comprises suture management means for managing a free end of a suture attached to a bone anchor disposed in the distal end of the axial passageway, the suture management means comprising a recess defining a first surface and an elastomer disposed in the recess so as to yieldably engage the first surface, whereby a free end of a suture may be forced between the first surface and the elastomer and retained there until thereafter forceably withdrawn.

In another form of the invention, the installation tool comprises:

a shaft comprising a first portion having a first cross-section, a second portion having a second cross-section less than the first cross-section, a shoulder defined by the intersection of the first and second portions, a third portion having a third cross-section less than the first cross-section, and a frustoconical shoulder defined by the intersection of the first and third portions;

a shaft housing adapted to slidingly receive the shaft, the shaft housing having a proximal cylindrical portion including an annular rib positioned a predetermined distance from a proximal end thereof, a fluted finger grip, and a stem extending distally from the fluted finger grip, the stem including a threaded portion and terminating in a chamfered nose;

a shaft handle adapted to fixedly receive the proximal end of the shaft, the shaft handle comprising a slotted cylindrical portion having an inwardly facing lip disposed on a distal end thereof, the slotted cylindrical portion further including four slots, each of the slots being circumferentially positioned in spaced-apart relation thereby defining four fingers adapted for gripping the annular rib of the shaft housing, a slotted flange disposed at a proximal end of the slotted cylindrical portion, the slotted flange having four slots each circumferentially disposed in spaced-apart relation, and a T-shaped post extending from a proximal surface of the slotted flange and adapted for retaining a free end of a suture, the T-shaped post comprising a central column having a hole adapted for fixedly receiving the proximal end of the shaft and a flange disposed at a proximal end of the central column, the central column extending distally from a flat inner surface of the flange;

a rubber grommet disposed around the central column and adapted to releasably hold a length of suture attached to the suture anchor;

a sleeve for slidingly receiving the shaft, the sleeve comprising a proximal end and a distal end, the proximal end including an annular groove positioned a predetermined distance from a proximal end surface thereof, and the sleeve including a pair of lateral passageways communicating with the central lumen of the sleeve adjacent the distal end, with the central lumen being of reduced diameter adjacent the distal end; and a sleeve handle comprising a proximal portion terminating in a flat proximal end, a distal portion terminating in a rounded distal end, and a bore extending between the proximal end and the rounded distal end, the sleeve handle being adapted for slidingly receiving the sleeve, the proximal portion of the sleeve handle further including a threaded counterbore adapted for releasably fastening the threaded portion of the stem, releasable locking means for releasably engaging the annular groove formed on the proximal end of the sleeve whereby the sleeve can be releasably secured to the sleeve handle, and the sleeve handle further including finger grip depressions disposed in opposing circumferential relation thereon and adapted to receive the thumb and fingers of a user during installation of the suture anchor.

The novel bone anchor installation tool can be used in the following manner to deploy the novel bone anchor in bone. First, the suture anchor is positioned at least partially within the distal end of the sleeve's axial passageway, with the bone anchor's barbs extending out through the installation tool's lateral passageways. Then the installation tool has its shaft positioned in its first retracted position, if it is not already in this position. Next, the proximal end of the sleeve is attached to the sleeve handle, and the free end of a suture (attached to the suture anchor) is positioned between the aforementioned first surface and elastomer so as to hold it to the tool. Then the distal end of the installation tool is positioned against the top surface of a bone having a hole formed therein, with the suture anchor being aligned with the hole. Next, the installation tool's shaft is moved from its first retracted position to its second extended position so as to deploy the suture anchor in the bone. Finally, the free end of the suture is removed from between the aforementioned first surface and the elastomer.

BRIEF DESCRIPTION OF THE DRAWINGS

These and other objects, features and advantages of the present invention will be more fully disclosed in, or rendered obvious by, the following detailed description of the preferred embodiments of the invention, which are to be considered together with the accompanying drawings wherein like numbers refer to like parts and further wherein:

FIG. 1 is a side view in elevation of a novel bone anchor formed in accordance with the present invention;

FIG. 2 is an end view showing the distal end of the bone anchor;

FIG. 3 is an end view showing the proximal end of the bone anchor;

FIG. 4 is a side view in section, showing the anchor's housing;

FIG. 5 is an end view showing the distal end of the anchor's housing;

FIG. 6 is an end view showing the proximal end of the anchor's housing;

FIG. 12 is a side elevational view of a fully assembled installation tool formed in accordance with the present invention, wherein the installation tool's shaft is in its first retracted position;

FIG. 13 is a side elevational view of the same fully assembled installation tool, wherein the installation tool's shaft is in its second extended position;

FIG. 15 is a side elevational view, partially in section, of a sleeve which constitutes part of the installation tool;

FIG. 16 is a side elevational view of the same sleeve, but with the sleeve having been rotated 90 degrees from the position shown in FIG. 15;

FIG. 17 is a side elevational view of a sleeve handle which constitutes part of the installation tool;

FIG. 18 is a bottom view of the sleeve handle;

FIG. 19 is an end view showing the proximal end of the sleeve handle;

FIG. 20 is a side view of a spring latch which is attached to the sleeve handle;

FIG. 21 is an end view of the distal end of the same spring latch;

FIG. 22 is a bottom view of the same spring latch;

FIG. 23 is a side elevational view of a shaft which constitutes part of the installation tool's shaft subassembly;

FIG. 24 is a side elevational view of a shaft housing which constitutes part of the installation tool's shaft subassembly;

FIG. 25 is a cross-sectional view taken along line 25—25 of FIG. 24;

FIG. 26 is an end view showing the proximal end of the shaft housing;

FIG. 27 is a side view in section of a shaft handle which constitutes part of the installation tool's shaft subassembly;

FIG. 28 is an end view showing the proximal end of the shaft handle;

FIG. 29 is a side view partially in section showing a bone anchor installed in the distal end of the bone anchor installation tool of the present invention;

FIG. 30 is a side view like that of FIG. 29, except that none of the drawing is in section and the bone anchor and installation tool have been rotated 90 degrees from the positions shown in FIG. 29;

DETAILED DESCRIPTION OF THE PREFERRED EMBODIMENTS

Figure 7:
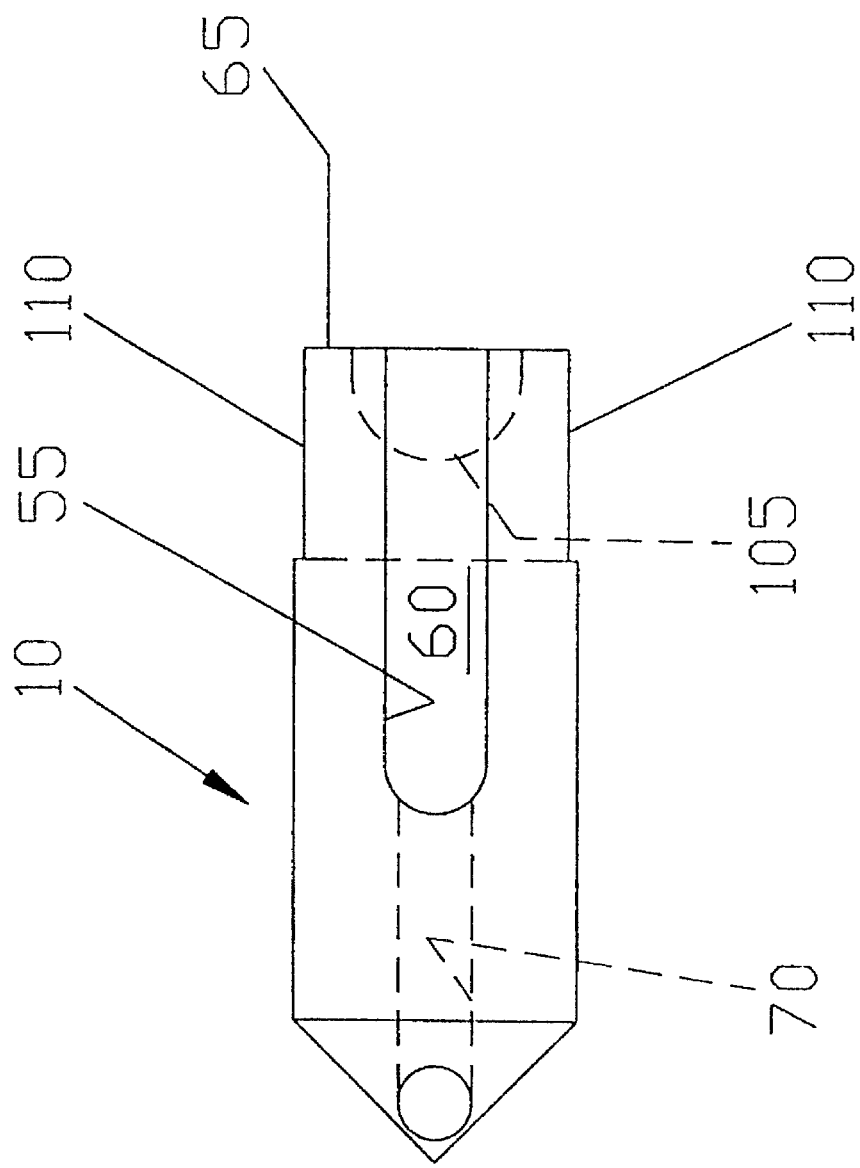
FIG. 7 is a side view in elevation of the anchor's housing, with the anchor having been rotated 90 degrees from the position shown in FIG. 4.
Figure 8:
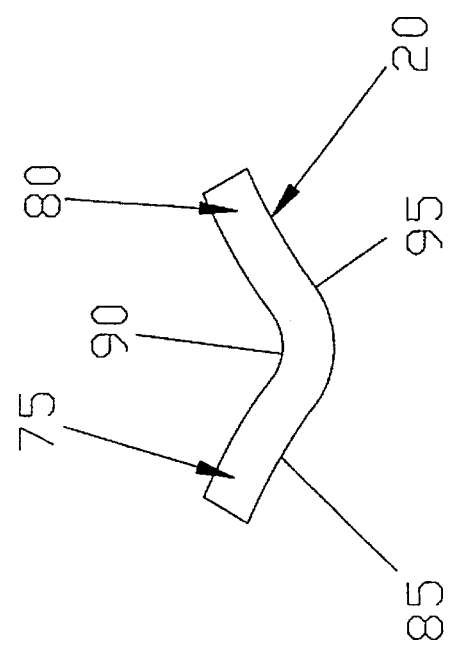
FIG. 8 is a side view in elevation of one of the anchor's barbs.
Figure 9:
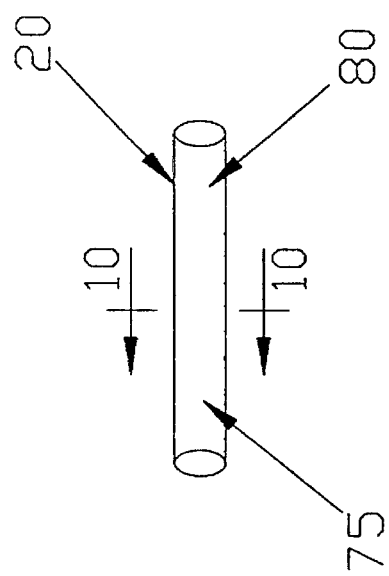
FIG. 9 is a top view of one of the anchor's barbs.
Figure 10:
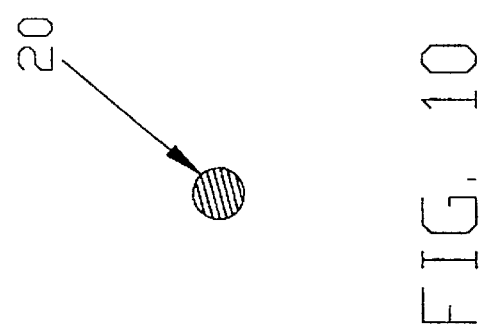
FIG. 10 is a cross-sectional view taken along line 10—10 of FIG. 9.

Turning first to FIGS. 1–11, a bone anchor 5 is shown which generally comprises a body 10 having a longitudinal axis 15 and at least two identical barbs 20. More specifically, and looking now at FIGS. 4–7 and 11, body 10 has a distal portion 25 having an inner end 30 and an outer end 35, and a proximal portion 40 having an inner end 45 and an outer end 50. Inner end 30 of distal portion 25 is connected to inner end 45 of proximal portion 40. Body 10 has a maximum cross-section (taken transverse to longitudinal axis 15) which is only slightly smaller than the diameter of a hole formed in a target bone, as will hereinafter be disclosed in greater detail. Body 10 is preferably formed out of 6AL-4V ELI titanium, although other suitable materials may also be used.

At least two equally-circumferentially-spaced longitudinal channels 55 are formed in the exterior of body 10. Each of the longitudinal channels 55 extends from inner end 45 of proximal portion 40 to outer end 50 of proximal portion 40. In the anchor embodiment shown in the drawings, there are two such channels 55. In fact, there are always exactly as many channels 55 as there are barbs 20 on the anchor. Thus, in the embodiment shown in the drawings, inasmuch as there are two barbs 20 on body 10, there are also two channels 55. The floors 60 of channels 55 slant outwardly relative to the anchor's longitudinal axis 15 at an angle of between about 12 and 30 degrees. Longitudinal channels 55 extend all the way to, and open on, outer end 65 of proximal portion 40.

At least two longitudinal bores 70 extend through distal portion 25, parallel to longitudinal axis 15. Bores 70 communicate with channels 55. In the embodiment shown, there are two such bores 70. In fact, there are always exactly as many of these bores 70 as there are barbs 20 on the anchor, and hence exactly as many of these bores 70 as there are channels 55. One bore 70 communicates with each channel 55, so as to form a forward extension of that channel.

Looking next at FIGS. 1–3 and 8–11, barbs 20 are each formed from a curved length of wire having a first or inner end 75 and a second or outer end 80. Barbs 20 are formed out of a relatively strong, highly elastic material such as a pseudoelastic alloy. Preferably barbs 20 are formed out of a stress induced martensite (SIM) shape memory alloy (SMA) material. Such materials are readily available from Raychem Corporation of Menlo Park, Calif. and Shape Memory Applications, Inc. of Sunnyvale, Calif. among others. The first or inner ends 75 of barbs 20 are attached to the anchor's distal portion 25 so that the barbs extend axially and radially outward therefrom. Each barb 20 is capable of being elastically deformed to a substantially straight configuration when desired.

Figure 11:
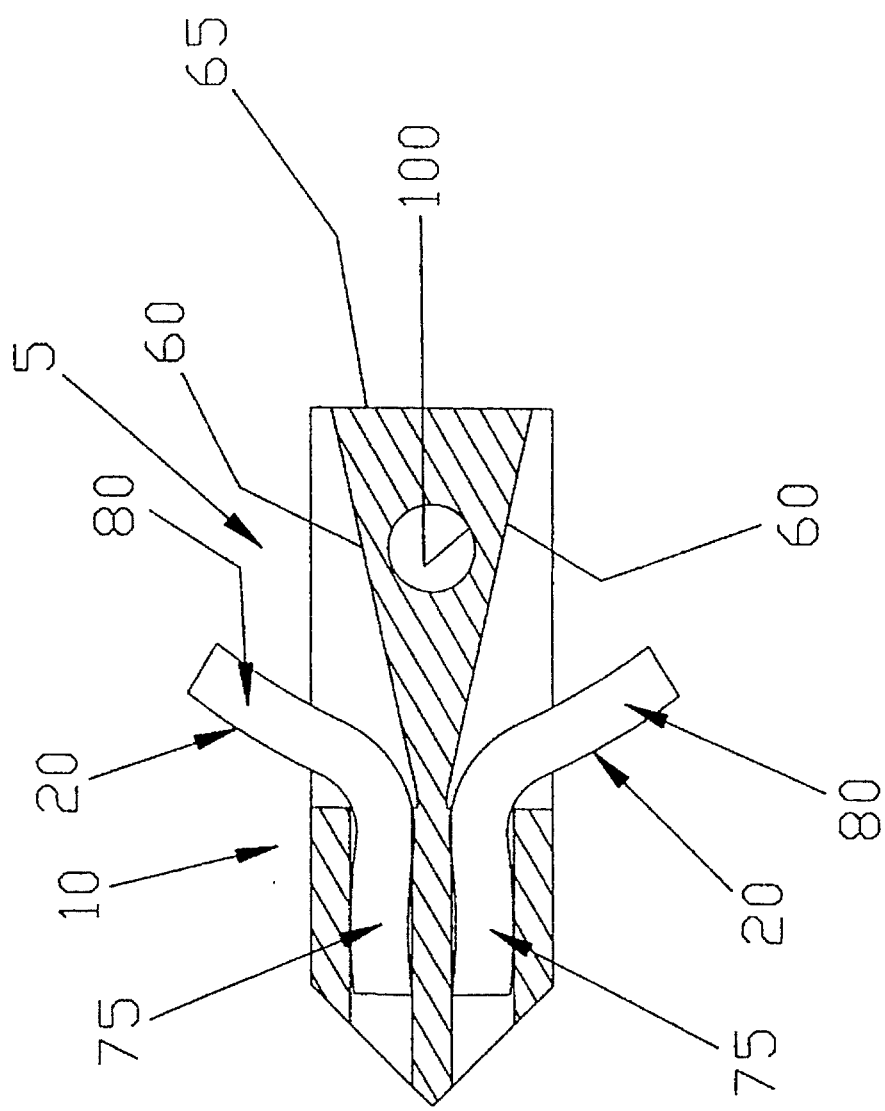
FIG. 11 is a side view, partially in section, showing two barbs disposed in the anchor's housing.

More particularly, each barb 20 comprises three distinct curves 85, 90 and 95 (FIG. 8) so as to assume a handlebar configuration in its normal unstressed state. Each barb 20 is attached to body 10 by forcing half of the barb into a bore 70 and allowing the remaining half of the barb to protrude out of a corresponding channel 55 (FIG. 11). The tendency of curved barbs 20 to return to their natural configuration after insertion into the straight bores 70 acts to securely hold the barbs in position within bores 70. The permanence of this engagement may be further assured by crimping distal portion 25 inwardly adjacent bores 70, or otherwise mechanically locking in place the portions of barbs 20 inserted into bores 70.

In view of the foregoing construction, it will be seen that barbs 20 will normally project axially rearward and radially outward from body 10, but they may also be bent inwardly under sufficient forces so that they can lie substantially flat against floors 60 of channels 55.

In this respect it is to be appreciated that barbs 20 and channels 55 are also sized and positioned relative to one another so that when barbs 20 are forced inwardly so as to lie against channel floors 60, all but the outermost portions 80 of barbs 20 will reside inside channels 55. Due to the inclined geometry of floors 60 at the proximal end of body 10, however, the outermost portions 80 of barbs 20 will remain at least slightly outboard of anchor body 10 even when barbs 20 lie against channel floors 60.

It is to be appreciated that, by forming barbs 20 with the foregoing handlebar configuration, the barbs will provide sufficient barb material for secure attachment to the anchor housing, and sufficient barb material for engaging the surrounding bone during anchor deployment, even when the anchor is formed with a very small size, e.g. with a body having a length on the order of 3.7 millimeters or so.

Still looking now at FIGS. 1–11, suture attachment means 100 are provided at proximal portion 40 of the anchor body. In the embodiment shown, suture attachment means 100 comprise a bore which extends through body 10, transverse to longitudinal axis 15 and between slanted floors 60 of channels 55 and adjacent to outer end 65 of proximal portion 40. The portion of bore 100 closest to outer end 65 of proximal portion 40 forms a smoothly contoured bearing surface 105 (FIG. 7) such that no sharp edges will be presented to a length of suture threaded through bore 100 and engaging surface 105, and such that a length of suture threaded through bore 100 and engaging surface 105 may be slid along that bearing surface 105 if desired after anchor 5 has been deployed in a bone hole. In addition, indented portions 110 (FIGS. 3, 6 and 7) preferably connect the proximal end of bore 100 to outer end 65 of proximal portion 40, thereby providing a protected pathway for the suture to emerge from bore 100 and extend proximally of the suture anchor.

It will be appreciated that by placing attachment means 100 at the proximal end of anchor 5 and locating attachment means 100 on the longitudinal axis of the anchor, any forces applied to the free ends of the suture once the suture anchor has been set in bone will not tend to induce rotational torque upon the anchor.

It is also to be appreciated that by inclining floors 60 of channels 55 at the proximal end of anchor body 10, sufficient body material will be provided about bore 100 so as to ensure the structural integrity of suture attachment means 100, while still allowing anchor 5 to be formed with the narrowest possible body diameter.

Looking next at FIGS. 12 and 13, a bone anchor installation tool 205 is shown which comprises a preferred embodiment of the present invention. Installation tool 205 generally comprises a shaft subassembly 210 (FIGS. 12–14), a sleeve 215 (FIGS. 12, 13, 15 and 16) and a sleeve handle 220 (FIGS. 12, 13 and 17–19).

Figure 14:
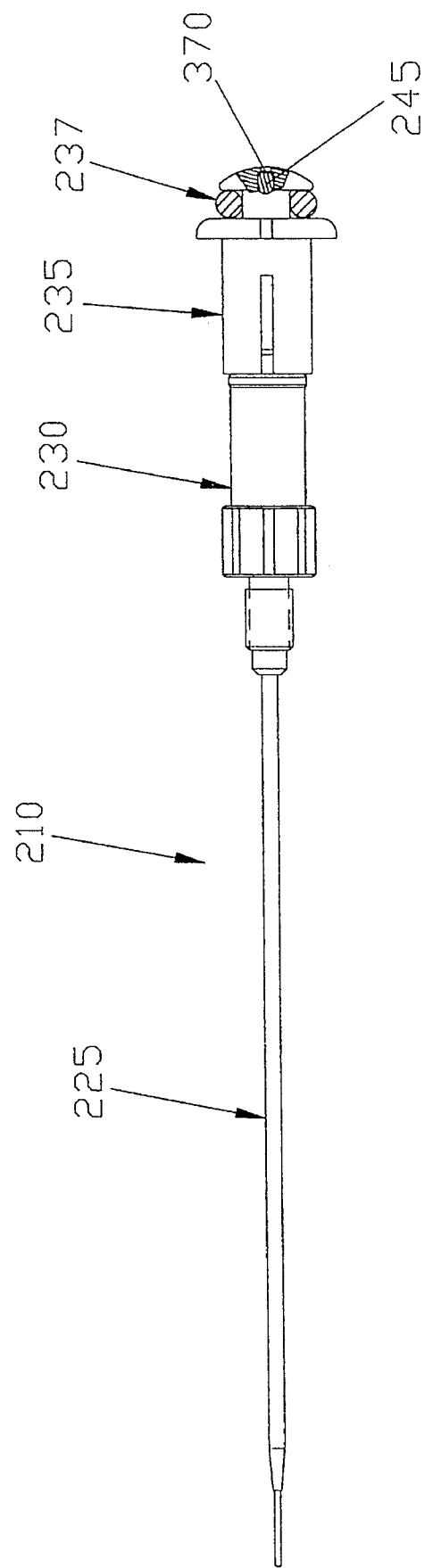
FIG. 14 is a side elevational view, in partial section, of the installation tool's shaft subassembly.

More particularly, and looking now at FIG. 14, shaft subassembly 210 generally comprises a shaft 225, a shaft housing 230, a shaft handle 235 and a rubber grommet 237.

Shaft 225 is shown in greater detail in FIG. 23. Shaft 225 comprises a first cylindrical portion 240 and a second cylindrical portion 245. Second cylindrical portion 245 has a smaller diameter than first cylindrical portion 240. First cylindrical portion 240 and second cylindrical portion 245 together define an annular shoulder 250. First cylindrical portion 240 is connected to a third cylindrical portion 251. Third cylindrical surface 251 has a smaller diameter than first cylindrical portion 240. First cylindrical portion 240 and third cylindrical portion 251 together define a frustoconical section 252. Third cylindrical portion 251 terminates in a distal end surface 255. Second cylindrical portion 245 terminates in a proximal end surface 260. Shaft 225 is formed so that the relatively thin third cylindrical portion 251 has a relatively short length relative to the remainder of the shaft.

Shaft housing 230 is shown in greater detail in FIGS. 24–26. Shaft housing 230 comprises a fluted finger grip 265 having a flat distal surface 267. A stem 270 extends distally away from the fluted finger grip's flat distal surface 267. Stem 270 includes a threaded portion 275 and terminates in a chamfered distal nose 280. Shaft housing 230 also comprises a cylindrical portion 285 extending proximally away from fluted finger grip 265. Cylindrical portion 285 includes an annular rib 290 and terminates in a flat proximal end surface 295. A central passageway 300 extends through shaft housing 230, from chamfered distal nose 280 of stem 270 to flat proximal end surface 295 of cylindrical portion 285.

Shaft handle 235 is shown in greater detail in FIGS. 27 and 28. Shaft handle 235 comprises a slotted cylindrical portion 305, a slotted flange 310 and a T-shaped post 315. More particularly, slotted cylindrical portion 305 comprises an inwardly facing lip 325 and four slots 330. Slots 330 are disposed in equally-circumferentially-spaced relation about the circumference of slotted cylindrical portion 305. In essence, slots 330 divide slotted cylindrical portion 305 into four longitudinally-extending fingers. Slotted flange 310 comprises four slots 335. Slots 335 are disposed in equally-circumferentially-spaced relation about the circumference of slotted flange 310. Slots 335 of slotted flange 310 are aligned with slots 330 of slotted cylindrical portion 305. Slotted flange 310 terminates in a flat distal surface 337 and in a proximal surface 340. The flange's proximal surface 340 is preferably rounded somewhat at its circumferential edge 342, adjacent to where proximal surface 340 meets flat distal surface 337. T-shaped post 315 comprises a cylindrical central column 345 and an annular flange 350. Flange 350 terminates in a rounded proximal surface 355 and in a flat distal surface 360. A rounded circumferential edge 365 is defined by the intersection of rounded proximal surface 355 and flat distal surface 360. A hole 370 extends axially through slotted flange 310 and into T-shaped post 315, and communicates with the interior of slotted cylindrical portion 305. Hole 370 is coaxial with, and communicates with, another hole 371 which opens on rounded proximal surface 355.

Rubber grommet 237 (FIGS. 12–14) comprises a toroidal shaped piece of elastomer adapted to be positioned on shaft handle 235. More particularly, rubber grommet 237 is adapted to be fit over the shaft handle's cylindrical central column 345 so as to be compressed between flat proximal surface 340 of slotted flange 310 and flat distal surface 360 of annular flange 350.

Shaft subassembly 210 is assembled as follows. First, the shaft's second portion 245 is passed through the shaft housing's central passageway 300 until the shaft housing's chamfered distal nose 280 engages the shaft's annular shoulder 250. Then shaft handle 235 is passed over the proximal end of shaft housing 230 until the proximal end of shaft 225 enters the shaft handle's hole 370. The proximal end of shaft 225 is then made fast in hole 370 by welding, using access hole 371. On account of the foregoing construction, shaft 225 and shaft handle 235 thereafter operate as a single unit, with shaft housing 230 being slidably captured on shaft 225 between the shaft's annular shoulder 250 and the shaft handle's distal surface 337, as will hereinafter be described in further detail. Once this has been accomplished, rubber grommet 237 is then mounted onto the shaft handle's cylindrical central column 345.

Looking next at FIGS. 15, 16 and 29–31, sleeve 215 comprises a distal portion 375 and a proximal portion 380. Distal portion 375 comprises two slots 385. Slots 385 are equally-circumferentially-spaced about the circumference of sleeve 215. Slots 385 open on the sleeve's distal end surface 390. The proximal portion of sleeve 215 includes an annular groove 395 and terminates in a proximal end surface 400. A bore 402 opens on distal end surface 390 and a coaxial counterbore 403 opens on proximal end surface 400. Bore 402 and counterbore 403 meet at an annular shoulder 406. Bore 402 is sized so that the shaft's third cylindrical portion 251 will make a close sliding fit within bore 402, and counterbore 403 is sized so that the shaft's first cylindrical portion 240 will make a close sliding fit within counterbore 403. Two lateral passageways 404 are formed in distal portion 375. Passageways 404 are equally-circumferentially-spaced about the circumference of sleeve 215. Passageways 404 extend at an acute angle to the longitudinal axis of sleeve 215 and communicate with bore 402. Preferably, the distal end of sleeve 215 is relieved slightly about its outer surface as shown at 407 so as to improve visibility at the surgical site.

Looking next at FIGS. 17–19, sleeve handle 220 comprises a distal portion 405 and a proximal portion 410. Distal portion 405 terminates in a rounded distal end surface 415 and proximal portion 410 terminates in a flat proximal end surface 420. Sleeve handle 220 also includes a bore 425 and a proximal counterbore 430. Counterbore 430 opens on the sleeve handle's flat proximal end surface 420. Bore 425 and counterbore 430 meet at an internal angled shoulder 435. The proximal portion of counterbore 430 is threaded at 440. A plurality of finger grip depressions 445 are formed in the outer surface of sleeve handle 220.

Sleeve handle 220 also includes a distal counterbore 448, a bottom recess 451, a threaded blind hole 454 extending upward into the body of sleeve handle 220 from bottom recess 451, and a thin slot 457 extending upward into the body of sleeve handle 220 from bottom recess 451. Counterbore 448 is coaxial with bore 425 and opens on rounded distal end surface 415. A spring latch 460 (FIGS. 12, 13 and 20–22) is disposed in bottom recess 451 so that its vertical leg 463 extends upward into thin slot 457 and its horizontal leg 466 extends along bottom recess 451, with the horizontal leg's hole 469 aligned with the sleeve handle's threaded blind hole 454. A screw (not shown) extends through the spring latch's hole 469 and into threaded blind hole 454 so as to attach the spring latch to the sleeve handle. The spring latch includes an elliptical opening 472 in its vertical leg 463 which intrudes across the sleeve handle's counterbore 448, whereby the spring latch can act as a releasable locking means for releasably capturing sleeve 215 to the sleeve handle, as will hereinafter be described in further detail.

The complete bone anchor installation tool 205 is assembled as follows. First, the assembled shaft subassembly 210 is passed distal end first through counterbore 430, bore 425 and counterbore 448 of sleeve handle 220, until chamfered distal nose 280 of shaft subassembly 210 enters counterbore 430 of sleeve handle 220. Shaft subassembly 210 is then rotated so that the shaft housing's threaded portion 275 engages threads 440 of sleeve handle 220. Shaft subassembly 210 is turned until the shaft housing's flat distal surface 267 engages the sleeve handle's proximal end surface 420.

Once shaft subassembly 210 has been connected to sleeve handle 220 in the foregoing manner, sleeve 215 can be connected to sleeve handle 220. This is done by depressing spring latch 460 so as to align its elliptical opening 472 with the sleeve handle's counterbore 448, and then passing the proximal end of sleeve 215 into the distal end of sleeve handle 220. Spring latch 460 can thereafter be released to engage the sleeve's annular groove 395 and thereby releasably bind sleeve 215 to the remainder of the installation tool.

When bone anchor installation tool 205 is assembled in the foregoing manner, its shaft 225 will be free to move between (i) a first retracted position (FIG. 12) wherein the shaft's annular shoulder 250 is substantially in engagement with the shaft housing's chamfered distal nose 280, and the shaft handle's inwardly facing lip 325 is on the proximal side of, and substantially in engagement with, the shaft housing's annular rib 290, and the shaft's distal end surface 255 is withdrawn into the interior of sleeve 215; and (ii) a second extended position (FIG. 13) wherein the shaft handle's flat distal end surface 337 is in engagement with the shaft housing's flat proximal end surface 295, and the shaft handle's inwardly facing lip 325 is on the distal side of, and substantially displaced from, the shaft housing's annular rib 290, and the shaft's distal end surface 255 protrudes a substantial distance beyond the sleeve's distal end surface 390.

Bone anchor installation tool 205 is preferably used to deploy a suture anchor such as the suture anchor 5 disclosed above, or a suture anchor of the sort disclosed in the aforementioned U.S. Pat. No. 5,217,486 and/or a suture anchor of the sort disclosed in the aforementioned U.S. patent application Ser. No. 08/197,927, i.e., bone anchor installation tool 205 is preferably used to deploy a suture anchor of the sort comprising (i) a generally cylindrical body, (ii) a pair of flexible barbs extending laterally out of the side of the body, and (iii) suture attachment means for attaching a length of suture to the body. Of course, bone anchor installation tool 205 may also be used to deploy other types of bone anchors in bone or other types of fasteners in a workpiece, so long as such bone anchor or fastener is compatible with the present invention.

Figure 31:
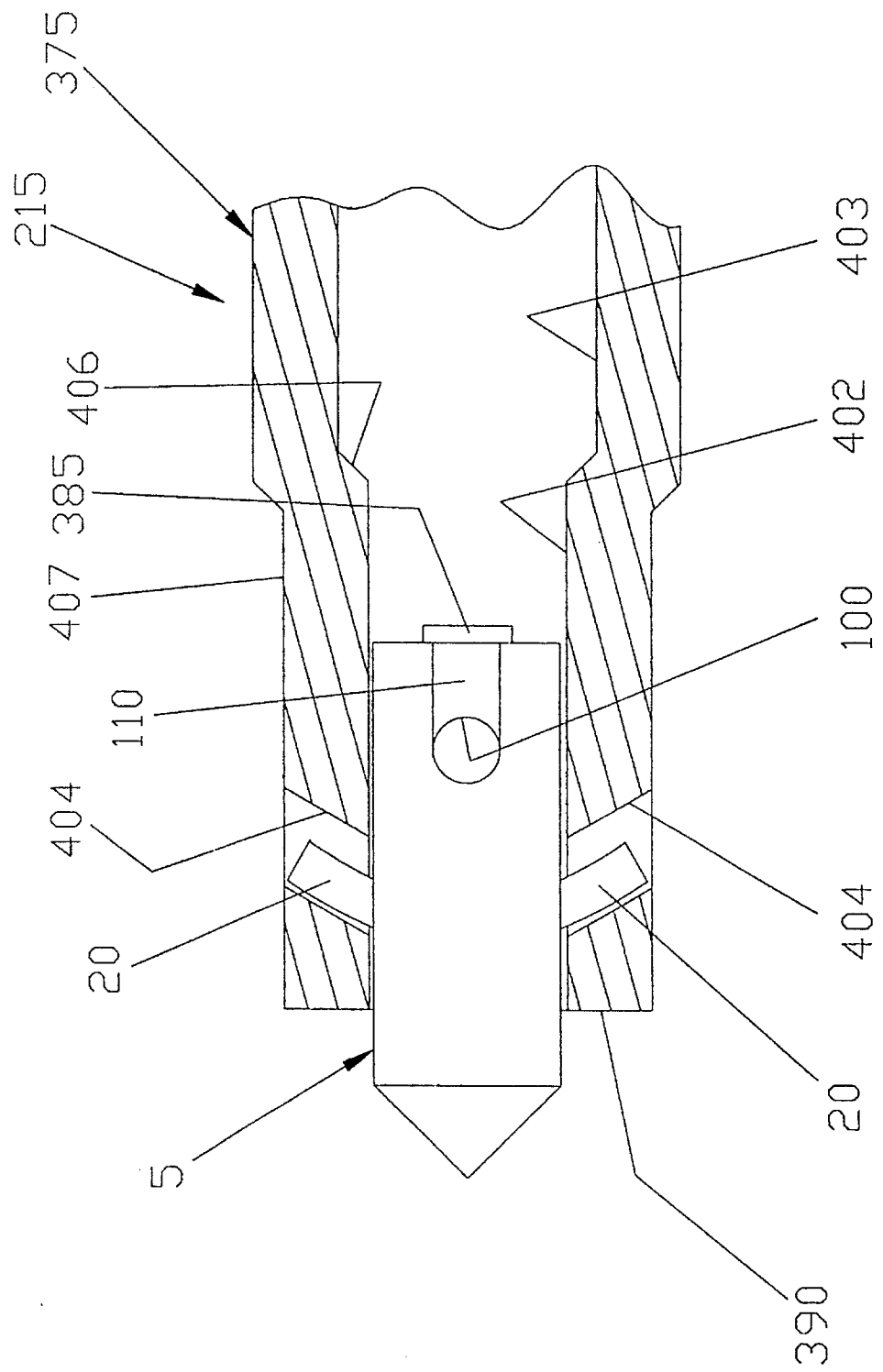
FIG. 31 is an enlarged distal end view corresponding to the view shown in FIG. 29.
Figure 33:
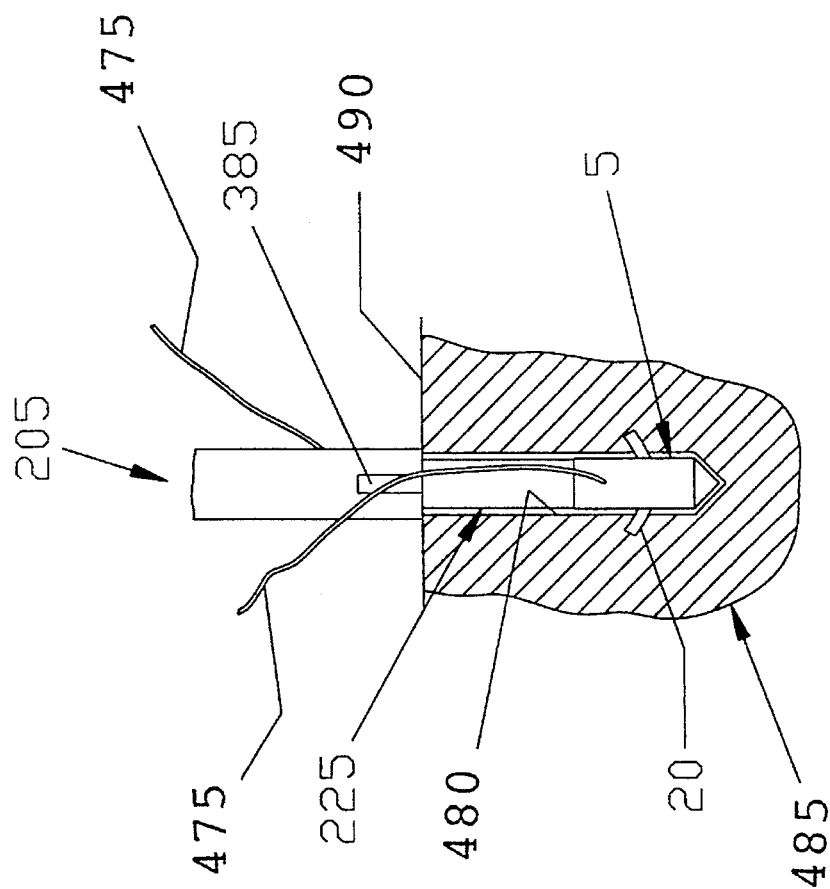
FIG. 33 is a view like that of FIG. 32, except that the bone anchor has been deployed in the bone.
Figure 32:
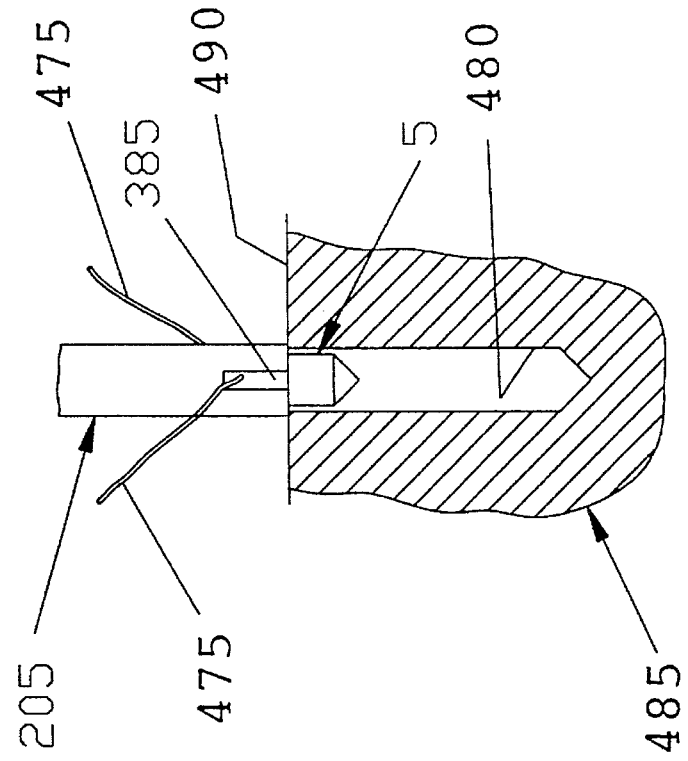
FIG. 32 is a side view showing the bone anchor and bone anchor installation tool, wherein the distal end of the installation tool is in engagement with the outer surface of a bone and the bone anchor is about to be deployed in that bone.

Bone anchor 5 and bone anchor installation tool 205 are intended to be used as follows. First, installation tool 205 is assembled so that its complete shaft subassembly 210 is connected to its sleeve handle 220, but without any sleeve 215 being connected to the sleeve handle. Then a bone anchor 5 is loaded into the proximal end of sleeve 215 and forced down the length of the sleeve until its barbs 20 project into lateral passageways 404 and its suture hole 100 is aligned with slots 385 (FIGS. 29–31). In this respect, it will be appreciated that the nature of the fit of barbs 20 in lateral passageways 404 will tend to keep anchor 5 from unintentionally separating from sleeve 215. A suture 475 (FIG. 32) is then threaded through slots 385 and suture hole 100 so as to connect suture 475 to the suture anchor.

Next, shaft 225 is positioned so that it is in its aforementioned first retracted position, wherein the shaft's annular shoulder 250 is substantially in engagement with the shaft housing's chamfered distal nose 280, and the shaft handle's inwardly facing lip 325 is on the proximal side of, and substantially in engagement with, the shaft housing's annular rib 290. Then a sleeve 215 (carrying a suture anchor 5 therein) is secured to sleeve handle 220 by depressing spring latch 460, inserting the proximal end of the sleeve into sleeve handle 220, and then releasing the spring latch. At this point the shaft's distal end surface 255 will reside within the interior of sleeve 215 (FIG. 12). It is to be appreciated that bone anchor installation tool 205 will be inclined to remain in its aforementioned first retracted position until it is thereafter forced to assume another position, inasmuch as the shaft housing's annular rib 290 will tend to inhibit passage of the shaft handle's inwardly facing lip 325.

Next, the two lengths of suture 475 are extended tautly back along the length of the installation tool and threaded through one or more of the shaft handle's slots 335 before being wound tightly around the shaft handle's cylindrical central column 345, in the space between rubber grommet 237 and the shaft handle's surface 340. The resilient engagement of rubber grommet 237 with the shaft's surface 340 thereafter serves to keep the two lengths of suture 475 securely in place at the proximal end of the installation tool, yet allows a surgeon to easily pull the two lengths of suture free from the installation tool when needed. Next, and looking now at FIG. 32, the installation tool is manipulated so as to position the distal portion of suture anchor 5 within the top of a hole 480 formed in a bone 485, with the distal end of sleeve 215 engaging the top surface 490 of the bone.

Suture anchor 5 can then be deployed in bone 485 by pressing on the shaft handle's proximal surface 355 so as to urge the installation tool's shaft 225 into its aforementioned second extended position. As this occurs, the shaft handle's inwardly facing lip 325 will be forced over the shaft housing's annular rib 290 as the shaft handle's flat distal end surface 337 moves into engagement with the shaft housing's flat proximal end surface 295 and the shaft's distal end surface 255 moves out of the sleeve's distal end. As a consequence of this action, suture anchor 5 will be driven out of the distal end of sleeve 215 and into bone 485, with the suture anchor's barbs 20 securing the anchor in place within the bone and with the two lengths of suture 475 extending back out of the bone hole to the installation tool. In this respect it will be appreciated that the relatively close fit between the shaft's third cylindrical portion 251 and the sleeve's bore 402, as well as the relatively short length of third cylindrical portion 251, will tend to ensure that the relatively thin third cylindrical portion of shaft 225 does not deform during anchor deployment. The two lengths of suture 475 may then be unwound from the installation tool before the installation tool is removed from the surgical site.

Another bone anchor may thereafter be deployed by the installation tool simply by dismounting sleeve 215 from sleeve handle 220 via spring latch 460, returning shaft 225 to its aforementioned first retracted position, and then repeating the aforementioned process, i.e., mounting a sleeve 215 (carrying a suture anchor 5 thereon) to the tool, etc.

In view of the very tiny nature of the bone anchors 5, it is envisioned that bone anchors 5 will be loaded on sleeves 215 at the point of manufacture, and then sleeves 215 (and their associated bone anchors) will be attached to the remainder of the installation tool in the field (e.g. in an operating room).

Advantages of the Present Invention

Numerous advantages are obtained by using the present invention.

For one thing, an improved bone anchor is provided.

For another thing, an improved bone anchor is provided which can be formed in a very, very small size.

Also, an improved bone anchor is provided which uses a new barb configuration so as to permit the bone anchor to be formed very, very small, yet provides sufficient barb material for secure attachment to the anchor body and for engaging the surrounding bone during anchor deployment.

Furthermore, an improved bone anchor is provided which is adapted to anchor suture to bone.

Also, an improved bone anchor installation tool is provided.

And an improved bone anchor installation tool is provided, wherein the installation tool is adapted to deploy bone anchors of the type adapted to anchor suture to bone.

Also, an improved bone anchor installation tool is provided, wherein the installation tool is adapted to provide improved suture management means for managing the free end or ends of a suture or sutures attached to the bone anchor.

Furthermore, an improved bone anchor installation tool is provided, wherein the installation tool is relatively easy to manufacture and relatively inexpensive to produce.

In addition, an improved method is provided for deploying a bone anchor in bone.

Still other advantages of the invention will be obvious to those skilled in the art.

Modifications of the Preferred Embodiment

It will, of course, be appreciated that certain modifications may be made to the foregoing preferred embodiment of the present invention without departing from the scope of the present invention.

Thus, for example, more than two slots 385 may be provided in the distal end of sleeve 215, where the installation tool is to be used in conjunction with a bone anchor of the sort having more than two free suture ends.

Furthermore, more or less than four slots 330 may be provided in slotted cylindrical portion 305, and/or more or less than four slots 335 may be provided in slotted flange 310.

Also, fluted finger grip 265 could be formed with an exterior surface which is knurled rather than fluted, or finger grip 265 could be formed with a relatively smooth surface if desired.

Additionally, suture could be held to the proximal end of the installation tool by wrapping it around cylindrical central column 345 between rubber grommet 237 and the shaft handle's flat surface 360, rather than between rubber grommet 237 and the shaft handle's surface 340.

These and other changes will be obvious to a person skilled in the art, and are considered to be within the scope of the present invention.

What is claimed is:

1. A bone anchor for attaching suture to a bone, said bone anchor comprising a body, at least two barbs fixed to said body, and suture attachment means on said body, said body having a longitudinal axis, a distal portion having an inner end and an outer end, and a proximal portion having an inner end and an outer end, wherein said inner end of said distal portion is connected to said inner end of said proximal portion;

said body further comprising at least two equally-circumferentially-spaced longitudinal channels extending from said inner end of said proximal portion to said outer end of said proximal portion, with the depth of said longitudinal channels gradually decreasing as said channels extend from said inner end of said proximal portion to said outer end of said proximal portion, and further wherein each of said longitudinal channels also has an associated bore communicating therewith, said bores extending from said inner end of said distal portion toward said outer end of said distal portion;

said barbs extending in equally-circumferentially-spaced relation to each other, and in equally spaced radial relation to the longitudinal axis, with one end of each of said barbs being disposed in one of said bores and the other end of said barb being substantially radially displaced from said housing, whereby each of said barbs is aligned with and extends out of one of said longitudinal channels, with each of said barbs being curved in its unstressed state, but being capable of being elastically deformed to a substantially straight configuration;

wherein each barb comprises three distinct curves so as to assume a handlebar configuration when it is in said unstressed state, with each of said barbs being attached to said body by positioning half of said barb in one of said bores with the other half of said barb protruding out of a corresponding one of said longitudinal channels; and said suture attachment means are formed in said proximal portion of said body and comprise a hole extending diametrically through said proximal portion of said body.

2. An installation tool for deploying a bone anchor in bone, said installation tool comprising:

a body having a distal portion and a proximal portion, said distal portion terminating in a distal end surface and said proximal portion terminating in a proximal end surface, and further wherein an axial passageway extends between said distal end surface and said proximal end surface, with said distal end of said axial passageway being sized to receive at least a portion of a bone anchor therein, and further wherein at least two lateral passageways extend through said body so as to intersect said axial passageway, each of said lateral passageways being adapted to receive a barb extending from said bone anchor when said bone anchor is disposed in said distal end of said passageway; and a shaft slidably disposed in said axial passageway, said shaft terminating in a distal end surface and being adapted to move between (i) a first retracted position wherein said distal end surface of said shaft is withdrawn sufficiently into the interior of said axial passageway so as to allow at least a portion of a bone anchor to be received within said distal end of said axial passageway, and (ii) a second extended position wherein said distal end surface of said shaft projects out of said distal end of said axial passageway.

3. An installation tool according to claim 2 wherein said installation tool further comprises suture management means for managing a free end of a suture attached to said bone anchor disposed in said distal end of said axial passageway, said suture management means comprising a recess in said tool defining a first surface, and an elastomer disposed in said recess to yieldably engage said first surface, whereby to cooperatively receive the free end of the suture between said first surface and said elastomer and retain the free end of the suture until it is forceably withdrawn.

4. An installation tool for deploying a bone anchor, said installation tool comprising:

a shaft comprising a first portion having a first cross-section, a second portion having a second cross-section less than said first cross-section, a shoulder defined by the intersection of said first and said second portions, a third portion having a third cross-section less than said first cross-section, and a frustoconical shoulder defined by the intersection of said first and third portions;

a shaft housing adapted to slidingly receive said shaft, said shaft housing having a proximal cylindrical portion including an annular rib positioned a predetermined distance from a proximal end thereof, a fluted finger grip, and a stem extending distally from said fluted finger grip, said stem including a threaded portion and terminating in a chamfered nose;

a shaft handle adapted to fixedly receive a proximal end of said shaft, said shaft handle comprising a slotted cylindrical portion having an inwardly facing lip disposed on a distal end thereof, said slotted cylindrical portion further including four slots, each of said slots being circumferentially positioned in spaced-apart relation thereby defining four fingers adapted for gripping said annular rib of said shaft housing, a slotted flange disposed at a proximal end of said slotted cylindrical portion, said slotted flange having four slots each circumferentially disposed in spaced-apart relation, and a T-shaped post extending from a proximal surface of said slotted flange and adapted for retaining a free end of a suture, said T-shaped post comprising a central column having a hole adapted for fixedly receiving said proximal end of said shaft and a second flange disposed at a proximal end of said central column, said central column extending distally from a flat inner surface of said second flange;

a rubber grommet disposed around said central column and adapted to releasably hold a length of suture attached to said suture anchor;

a sleeve for slidably receiving said shaft, said sleeve comprising a proximal end and a distal end, said proximal end including an annular groove positioned a predetermined distance from a proximal end surface, and said sleeve including a pair of lateral passageways communicating with the central lumen of said sleeve adjacent the distal end, with said central lumen being of reduced diameter adjacent said distal end; and a sleeve handle comprising a proximal portion terminating in a flat proximal end, a distal portion terminating in a rounded distal end, and a bore extending between said proximal end and said rounded distal end, said sleeve handle being adapted for slidingly receiving said sleeve, said proximal portion of said sleeve handle further including a threaded counterbore adapted for releasably fastening said threaded portion of said stem, releasable locking means for releasably engaging said annular groove formed on said proximal end of said sleeve whereby said sleeve can be releasably secured to said sleeve handle, and said sleeve handle further including finger grip depressions disposed in opposing circumferential relation thereon and adapted to receive a thumb and fingers of a user during installation of said suture anchor.

5. An installation tool according to claim 4 wherein said shaft's first and second cross-sections are cylindrical.

6. An installation tool according to claim 4 wherein said fluted finger grip comprises a plurality of circumferentially disposed flutes.

7. An installation tool according to claim 4 wherein four slots are circumferentially positioned in spaced-apart relation in said slotted flange and are in aligned relation to said slots in said slotted cylindrical portion of said shaft handle.

8. An installation tool according to claim 4 wherein said second flange of said shaft handle further comprises a rounded proximal surface and a flat distal surface so as to define a rounded circumferential edge therebetween.

9. An installation tool according to claim 4 wherein said proximal end of said shaft is welded in said hole of said shaft handle.

10. A system for deploying a suture anchor in a hole formed in a bone, said system comprising:

(i) a suture anchor comprising a generally cylindrical body, a pair of flexible barbs extending laterally out of the side of said body, and suture attachment means disposed on said body for attaching a length of suture to said body; and (ii) an installation tool for deploying said suture anchor in bone, said installation tool comprising:

a body having a distal portion and a proximal portion, said distal portion terminating in a distal end surface and said proximal portion terminating in a proximal end surface, and further wherein an axial passageway extends between said distal end surface and said proximal end surface, with a distal end of said axial passageway being sized to receive therein at least a portion of said suture anchor, and further wherein at least two lateral passageways extend through said tool body so as to intersect said axial passageway, whereby each of said barbs is received by one of said lateral passageways when said bone anchor is disposed in said distal end of said passageway;

a shaft slidably disposed in said axial passageway, said shaft terminating in a distal end surface and being adapted to move between (i) a first retracted position wherein said distal end surface of said shaft is withdrawn sufficiently into the interior of said axial passageway to allow at least a portion of said suture anchor to be received within said distal end of said axial passageway, and (ii) a second extended position wherein said distal end surface of said shaft projects out of said distal end of said axial passageway; and suture management means for managing a free end of a suture attached to said suture anchor when said suture anchor is disposed in said distal end of said axial passageway, said suture management means comprising a recess in said tool defining a first surface, and an elastomer disposed in said recess so as to yieldably engage said first surface, whereby to cooperatively receive a free end of the suture between said first surface and said elastomer and retain the free end of the suture until it is forceably withdrawn.

11. A method for deploying a suture anchor in bone, said method comprising the steps of:

(1) providing a system for deploying a suture anchor in a hole formed in a bone, said system comprising:

(i) a suture anchor comprising a generally cylindrical body, a pair of flexible barbs extending laterally out of the side of said body, and suture attachment means for attaching a length of suture to said body; and (ii) an installation tool for deploying said suture anchor in bone, said installation tool comprising:

a body having a distal portion and a proximal portion, said distal portion terminating in a distal end surface and said proximal portion terminating in a proximal end surface, and further wherein an axial passageway extends between said distal end surface and said proximal end surface, with a distal end of said axial passageway being sized to receive therein at least a portion of said suture anchor, and further wherein at least two passageways extend through said tool body so as to intersect said axial passageway, whereby each of said barbs of said suture anchor is received by one of said lateral passageways when said suture anchor is disposed in said distal end of said passageway;

a shaft slidably disposed in said axial passageway, said shaft terminating in a distal end surface and being adapted to move between (i) a first retracted position wherein said distal end surface of said shaft is withdrawn sufficiently into the interior of said axial passageway to allow at least a portion of said suture anchor to be received within said distal end of said axial passageway, and (ii) a second extended position wherein said distal end surface of said shaft projects out of said distal end of said axial passageway; and suture management means for managing a free end of a suture attached to said suture anchor when said suture anchor is disposed in said distal end of said axial passageway, said suture management means comprising a recess in said tool defining a first surface, and an elastomer disposed in said recess so as to yieldably engage said first surface, whereby to cooperatively receive a free end of the suture and retain the free end of the suture until it is forceably withdrawn;

(2) positioning said shaft in said first retracted position;

(3) positioning a suture anchor at least partially within said distal end of said axial passageway, and positioning the free end of a suture attached to said suture anchor between said first surface and said elastomer;

(4) positioning said distal end of said installation tool against a top surface of a bone having a hole formed therein, with said suture anchor being aligned with said hole;

(5) moving said shaft from said first retracted position to said second extended position so as to deploy said suture anchor in said bone; and (6) removing said free end of said suture from between said first surface and said elastomer.

* * * * *